United States Patent
Schmitt

(10) Patent No.: US 6,944,269 B2
(45) Date of Patent: Sep. 13, 2005

(54) MEDICAL IMAGING EXAMINATION FACILITY

(75) Inventor: Thomas Schmitt, Forchheim (DE)

(73) Assignee: Siemens Aktiengesellschaft, Münich (DE)

( * ) Notice: Subject to any disclaimer, the term of this patent is extended or adjusted under 35 U.S.C. 154(b) by 325 days.

(21) Appl. No.: 10/307,798

(22) Filed: Dec. 2, 2002

(65) Prior Publication Data
US 2003/0108154 A1 Jun. 12, 2003

(30) Foreign Application Priority Data
Dec. 11, 2001 (DE) .......................................... 101 60 611

(51) Int. Cl.$^7$ ................................................. H05G 1/58
(52) U.S. Cl. ......................... 378/115; 378/62; 378/165
(58) Field of Search .......................... 378/62, 115, 165; 382/128, 130, 131, 132

(56) References Cited

U.S. PATENT DOCUMENTS 5,784,431 A * 7/1998 Kalend et al. ................ 378/65

FOREIGN PATENT DOCUMENTS

| DE | 38 23 251 | 1/1989 |
|----|-----------|--------|
| DE | 100 65 558 | 7/2001 |

* cited by examiner

Primary Examiner—Edward J. Glick
Assistant Examiner—Courtney Thomas
(74) Attorney, Agent, or Firm—Schiff Hardin LLP

(57) ABSTRACT

A medical imaging examination device has an X-ray source, a reception unit for receiving the X-rays that penetrate a patient, an operating device for operation of the examination device by an operator, and a memory device wherein images are or can be stored in electronically readable form. The images can be X-ray images registered in earlier examinations or images that simulate X-ray images. A selection device reads out one of the stored images out from the memory device dependent on a desired examination region of the patient and displays it on a display device before the examination of the examination region with X-rays. The operating personnel, possibly in conjunction with a control functionality of the examination device are thus provided with a visualization of an X-ray image to be anticipated.

13 Claims, 2 Drawing Sheets

MEDICAL IMAGING EXAMINATION FACILITY

BACKGROUND OF THE INVENTION

1. Field of the Invention

The present invention is in the field of medical imaging examination devices, for example X-ray exposure stations, X-ray fluoroscopy systems and computed tomography devices.

More specifically, the present invention is directed to an imaging medical examination device of the type having an X-ray source, a reception unit for receiving the X-rays that penetrate a patient, and an operating device for operation of the examination device by an operator.

2. Description of the Prior Art

For post-processing of medical images, German 38 23 251 discloses that the images from various diagnostic devices be saved in databanks via a network, the images being displayable at separate image presentation workstations via a network proceeding from said databanks.

German OS 100 65 558 discloses a medical diagnosis system having online real-time video training. The videos show an operator how, for example, a computed tomography apparatus or a magnetic resonance apparatus is to be operated.

SUMMARY OF THE INVENTION

An object of the present invention is to simplify the operation of a medical examination device for the user, particularly for the medical-technical personnel in a hospital.

This object is achieved in an examination apparatus of the type initially described, having a memory device wherein medical images are or can be stored in electronically readable form, a selection device that selects one of the stored images and reads it out from the memory device dependent on an examination region of the patient that the operator wants for a current examination, and a display device on which the image that has been read out can be displayed to the operator before the examination of the examination region with the X-rays.

The images stored in the memory device can be X-ray images registered in earlier examinations with the same apparatus or some other examination apparatus, or images that simulate X-ray images.

The examination device offers the operator a visualization or a simulation of the X-ray image to be expected. In the inventive examination apparatus, the operator, who must often implement examinations in rapid chronological succession during the course of a workday, is provided with visual information as to what can be anticipated as the examination result given examination of a specific examination region, and how this becomes visible in the X-ray image. The display device interacting with the memory device and the selection device is arranged, for example, in the spatial proximity of the operating device, so that the display device can be viewed by the operator operating the operating device. The display device thus assists the operator with X-ray images registered in earlier examination or with images that simulate X-ray images.

The selection device can be fashioned, for example, as a functional group or as a module in a computer that controls the examination device. The memory device may be a component of such a computer.

The reception unit for the reception of X-rays in the contest of invention can be, for example, an X-ray film-based reception unit arranged, for example, in a cassette, a tube-based reception unit, particularly with an image intensifier, or a semiconductor-based reception unit, for example a silicon-based solid-state detector.

Various embodiments provide different ways for the operator to inform the selection device of the desired examination region, so that the selection device can then automatically select an image.

In a first selection embodiment, the selection device undertakes the selection dependent on an input made at the operating device.

In particular, the selection device undertakes the selection dependent on a desired examination region that has been entered, particularly dependent on a desired organ. In other words: the operator specifies the examination region by means of an input.

At the beginning of a new examination, for example, the operator is shown an image of a human being on the display device at a user interface, and the operator specifies the examination region in this image. The specifying can occur, for example, by moving a mouse pointer to the examination region with subsequent clicking thereon. Alternatively, the definition ensues by touching a touch screen (key elements in front of a display surface).

In a preferred version of this embodiment, one or more position proposals for the reception unit are displayed, such as graphically, on the display device dependent on the desired examination region. This is particularly suited for instances wherein a number of beam paths through the examination region of the patient are medically meaningful.

The selection device preferably undertakes the selection of an image dependent on a positioning proposal selected via the operating device. A more refined image selection is thus possible compared to image selection that is undertaken dependent only on the examination region. The selection of one of the positioning proposals that is presented can occur like the specifying of the examination region, particularly with the assistance of a mouse pointer or a touch screen.

The various positioning proposals are presented, for example simultaneously, on the basis of a displayed portion of the patient in one part of the display device and the image appertaining to the respectively selected positioning proposal in another part of the display device. The operator then has the possibility of successively viewing the different images by successively selecting the various positioning proposals and finding a positioning that is beneficial for the pending examination.

Particularly for this purpose, the display device can include multiple picture screens. Alternatively, it can be fashioned as a split screen.

In a second selection embodiment, the selection device undertakes the selection dependent on the current position of the reception unit and/or dependent on the current position of the patient. For example, the operator moves the reception unit to the desired examination region and aligns it as wanted. The selection device takes both the location as well as alignment of the reception unit into consideration and—within certain pre-defined tolerance limits—selects an image to be anticipated. Given a change in position or direction of the reception unit, the appertaining image to be anticipated can thereby be respectively automatically followed-up.

In a preferred version of this embodiment, the selection device modifies the image that is read out dependent on an input of a device parameter undertaken at the operating device before the modified image is displayed at the display device. This offers the advantage that the integrated help function of the inventive examination apparatus is fashioned especially true-to-life. Compared to a procedure wherein different images would also be stored for different settings of a device parameter, there is also the advantage of a lower memory capacity. As a result of the input of the device parameter being accomplished in the image, the operator is provided with an impression of what would be produced in the examination result given an actual drive of the examination apparatus with this device parameter.

The device parameter preferably is a tube voltage of the X-ray source, a tube current of the X-ray source, a switching time of the X-ray source and/or a radiation quantity of the X-ray source.

For example, the image that is read out can be varied as to brightness, contrast and/or only in a partial region. In particular, the variation ensues pixel-by-pixel, with the intensity and/or color allocated to each pixel being modified. For example, a modification of the brightness of the image that is read out simulates a modification of the tube current. Filters that can be introduced into the beam path, such as organ filters such as, for example, a hilus filter, can be simulated by only a partial region of the image that is read out being modified.

The examination device preferably is fashioned such that the settings of the device parameter undertaken during the simulation or preview can be accepted for the actual drive of the examination device by means of a confirmation command on the part of the operator, without having to re-enter or redefine the device parameter.

In a third selection embodiment, the examination device has a sensor for acquiring a two-dimensional image of the patient. Optionally a height profile can be acquired as well, so that a three-dimensional image, of the patient is acquired. The selection device is configured such that, employing initial data of the sensor, the length ("height"), the thickness and/or the sex of the patient can be evaluated. The selection device, dependent on the evaluation, undertakes the selection of one of the stored images and/or modifies the image that is read out before it is displayed on the display device.

This third selection embodiment of the selection device can be employed as an additional selection criterion after selection of a desired examination region. As a result, an especially true-to-life image for the desired examination region can be selected from a number of images stored in the memory device.

As described above, the modification of the image that is read out can ensue as to brightness, contrast and/or only in a partial region.

In another preferred embodiment the image that is read out can be displayed simultaneously on the display device together with symbols in a relationship that can be perceived by the operator. Available device settings are selectable or controllable via these symbols. This offers the advantage that the help function established by the stored images can be embedded into the control function of the examination device in a way that is especially user-friendly for an operator.

The relationship of the displayed image to the control function can be perceived particularly when the image is displayed immediately before or after a user interface or simultaneously with a user interface, preferably embedded in such a user interface. The device settings can be selected on the user interface, for example with a mouse pointer.

DESCRIPTION OF THE PREFERRED EMBODIMENTS

Figure 1:
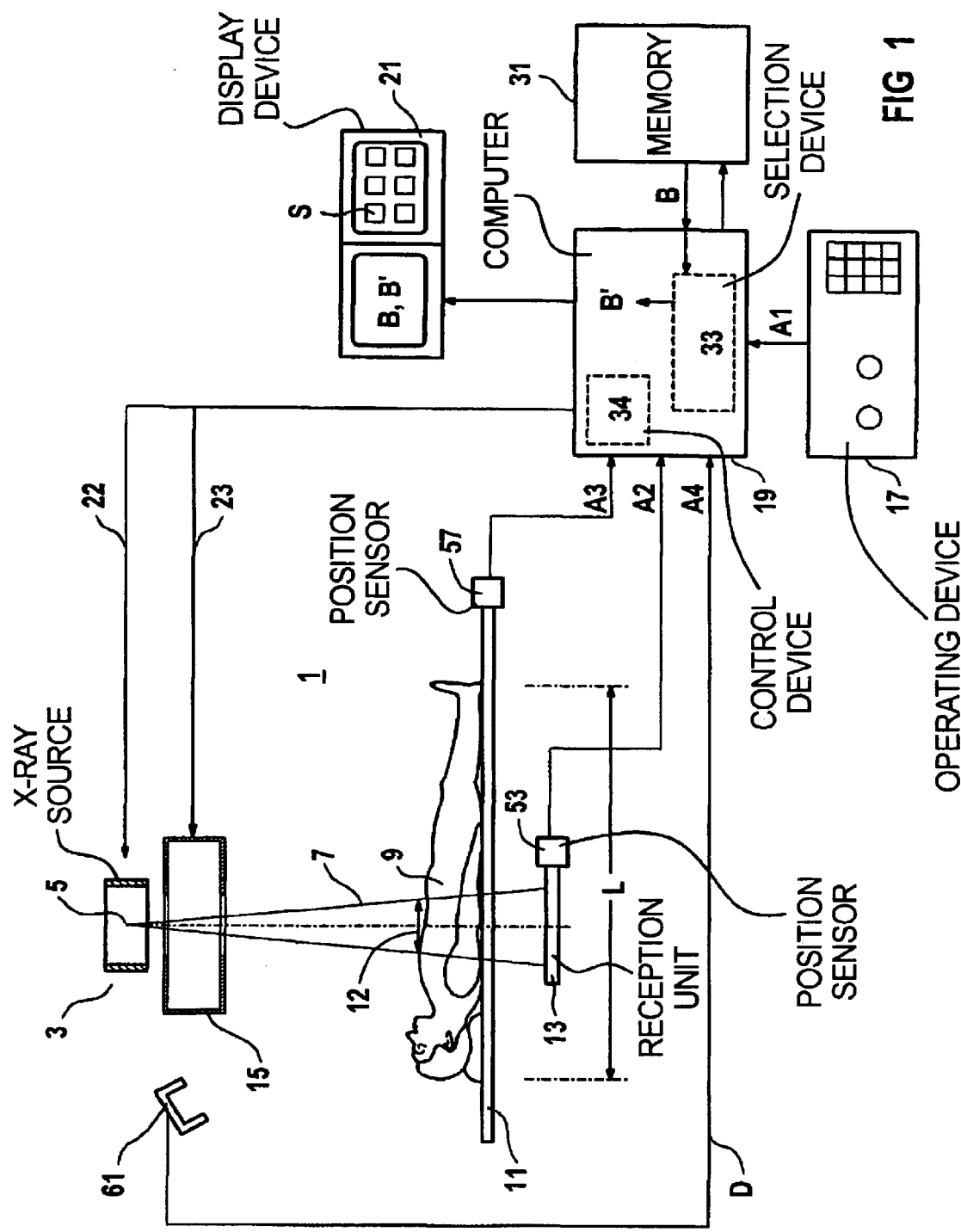
FIG. 1 is a schematic, overall view of an examination device of the invention.

FIG. 1 shows a medical examination device fashioned as a conventional X-ray apparatus (but with the inventive features described below), having an X-ray tube as an X-ray source 3, a ray beam 7 emanating from the focus 5 thereof and transirradiating a patient 9 lying on a support mechanism 11. In particular, an examination region 12 is transirradiated that is determined by selection of the positions of the patient 9 and the X-ray source 3 and the position of a reception unit 13. A filter and diaphragm device 15 is allocated to the X-ray source 3 for the correct gating of the examination region 12. In the illustrated example, the reception means 13 is an X-ray cassette with an X-ray film and an intensifier foil.

An operating device 17 is present for the operation of the examination device 1. The operating device 17 influences a computer 19 that controls the X-ray source 3 and the filter and diaphragm device 15—via the illustrated lines 22, 23—as well as drive unit (not explicitly shown) for the reception unit 13 and the support mechanism 11—via lines that are likewise not explicitly shown.

The computer 19 is also in communication with a display device 21 that is composed of two picture screens. Given an electronically readable reception unit 13, an actually, i.e. currently, acquired X-ray image could be displayed on the display device 21. The display device 21 also serves for the presentation of user interfaces via which inputs can be made with, for example, a touch screen or a mouse pointer. The display device 21 may alternatively have only a single monitor (for example, as a split screen) that, in addition to displaying a user interface, displays images B that assist in the operation.

A memory device 31 is allocated to the computer 19 either locally or via a data network, for example an Internet or Intranet. Digitalized X-ray images B of earlier examinations at the same examination device 1 or at another device of the same type, i.e. examinations of the same patient 9 or of other patients or of model persons, are saved in the memory device 31. The memory device 31 contains an archive of X-ray images B for different examination regions 12, for different positions of the reception means 13, for different sizes and for different sexes of the patient 9. For example, the following images B can be stored:

| Examination Region | Receiver Position (particularly alignment) | Size | Sex |
|---|---|---|---|
| Thoracic spinal column | from front to back | adult | male |
| Thoracic spinal column | from front to back | child | male |
| Thoracic spinal column | from front to back | adult | female |
| Thoracic spinal column | from front to back | child | female |
| Thoracic spinal column | Laterally | adult | male |
| Thoracic spinal column | Laterally | child | male |
| Thoracic spinal column | laterally | adult | female |
| Thoracic spinal column | laterally | child | female |
| Bridge of the nose | laterally | . . . | . . . |
| . . . | . . . | . . . | . . . |

By loading suitable software into the computer 19, a selection device 33 that reads one of the stored images B out of the memory device 31 dependent on a desired examination region 12 of the patient 9 is formed as a functional group therein in addition to a control device 34 that effects the device control or setting.

The selection is possible according to different versions:
1. Selection A1 dependent on a desired examination region 12 input at the operating device 17.

Figure 2:
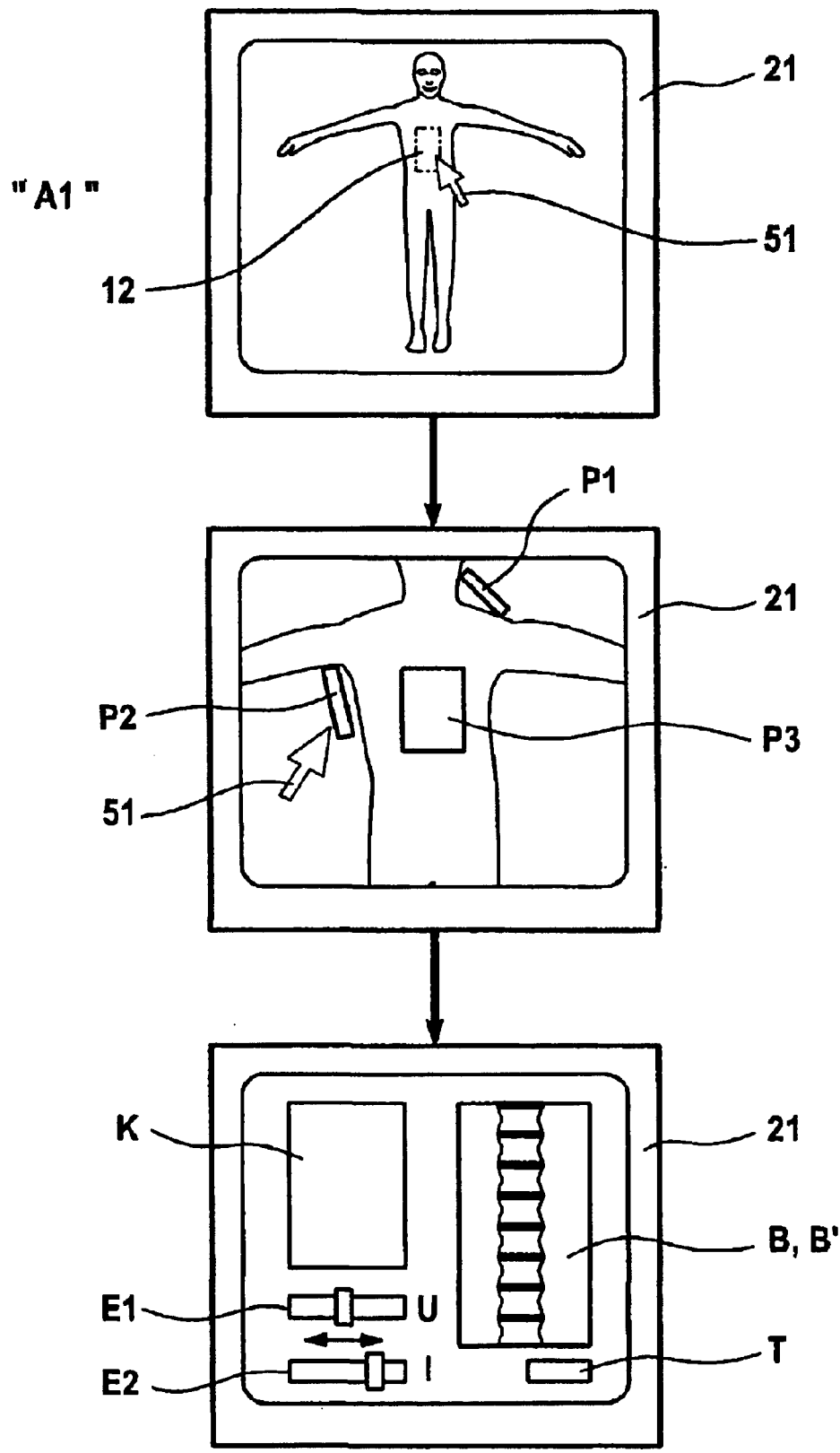
FIG. 2 illustrates an exemplary image sequence on a display device of the examination device of FIG. 1.

This selection possibility A1 is shown in detail in FIG. 2. At the beginning of the examination, the operator is first shown an image of a human being on the display device 21, the operator then specifying the desired examination region 12 thereon by moving a pointer 51 mixed into the display device 21. After specifying the examination region, the graphic view of an enlarged portion of the human being shown in the middle region of FIG. 2 appears for the operator, with various positioning proposals P1, P2, P3 for the reception unit 13 simultaneously mixed in. The operator can seek one of these positioning proposals P1, P2, P3 with the pointer 51 and then receives the view shown in the lower part of FIG. 2. The movement of the pointer 51 ensues, for example, by means of a computer mouse allocated to the operating device 17. Alternatively, the selection of the examination region 12 or of one of positioning proposals ensues with the assistance of a touch screen (parts physically allocated to the display device 21 considered in this case as components of the operating device 17).

The image B that is read out from the memory device 31 and that is to be anticipated for the selected examination region 12 and the selected positioning proposal P1, P2, P3 is shown at the right in the lower part of FIG. 2. Help positions for the operating personnel are written in a comment region to the left thereof, for example relating to the radiation protection, to support aids that are to be applied or to the support of the patient in and of itself. Adjustment buttons E1, E2 for the tube voltage U (in kV) or for the tube current I (in mA) are shown therebelow. The influence of such modifications on the image B can be tested as a preview or simulation by moving corresponding slides at the adjustment buttons E1, E2. To this end, the selection device 33 modifies the image B as to brightness and/or contrast and displays this as a modified image B'. Additionally, setting buttons can be present for diaphragm or filter functions of the filter and diaphragm device 15, whereby a corresponding filter or diaphragm effect is simulated, for example, by modifying a partial region of the image B. A setting button for a radiation quantity (in mAs) can also be present.

When the operator has adequately tested the device parameters, these can be accepted as actual device settings for the following examination of the patient 9 by pressing a confirmation key T at the operating device 17.

2. Selection A2, A3 dependent on the respectively current position of the reception unit 13 and/or on the respectively current position of the patient 9.

In the exemplary illustration of this version the selection device 33 is supplied with the output signals of a first position sensor 53 for the reception unit 13 and or the output signal of a second position sensor 57 for the support mechanism 11.

The operator moves the reception unit 13 to the desired examination region 12, and the X-ray source 3 can be automatically readjusted by the control device 34. The selection device 33 then automatically selects an X-ray image B to be anticipated in this examination region and visibly displays it for the operating personnel on the display device 21.

Given a suitable fashioning of the first position sensor 53, the measured alignment of the reception unit 13 can also be utilized in the image selection, for example in order to make a selection. From second column in the above Table. In addition to the location coordinates (x, y, z), the position sensor 53 then also determines inclination data.

A further refinement of the image selection corresponding to columns 3 and 4 in the above Table can be undertaken by means of corresponding inputs by the personnel via the operating device 17. As an alternative, the automated procedure described below is possible.

3. Selection A4 dependent on output data D of a sensor.

The examination device 1 has a sensor 61 fashioned as 3D chip with which the patient 9 and the reception unit 13 can be acquired. Output data D of the sensor 61 are supplied to the selection device 33, wherein the size L, the sex and the thickness of the patient 9 are calculated, for example by means of a pattern recognition algorithm. The selection device 33 selects that X-ray image B to be expected given this position with the spatial arrangement acquired by the sensor 61, with the length L, the thickness and the sex of the patient 9 additionally taken into consideration. The corresponding image is presented at the display device 21.

A particular advantage of the invention is that the image B read out according to one of the various possibilities can be presented on the display device 21 in a relationship with a control functionality of the control device 34 that can be perceived by the operating personnel. As shown in FIG. 1, for example, a graphic user interface with symbols S via which the possible device settings are selectable or controllable can be displayed on the right-hand picture screen of the display device 21. Simultaneously therewith, the image B or B' to be expected is visible for the operating personnel in the left picture screen. For example, the presentation of the image B or B' can be embedded into an organ program.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical imaging examination device comprising:
    an X-ray source which emits X-rays adapted to penetrate a patient;
    a reception unit on which said X-rays are incident after penetrating said patient;
    an operating device adapted to receive inputs from an operator for operating at least said X-ray source;
    a memory containing a plurality of images stored in electronically readable form, said images being selected from the group consisting of previously-registered X-ray images and simulation images which simulate X-ray images;
    a selection device connected to said memory for selecting and reading out one of said images from said memory dependent on an examination region of said patient for a current examination; and
    a display device connected to said memory for displaying said one of said images before said current examination.

2. An examination device as claimed in claim 1 wherein said selection device selects said one of said images dependent on an input identifying said examination region via said operating device.

3. An examination device as claimed in claim 2 wherein said operating device receives said input as a designation of an organ for said current examination.

4. An examination device as claimed in claim 3 wherein, dependent on said input via said operating device, said operating device causes a plurality of position proposals for said reception unit to be displayed at said display device dependent on said examination region.

5. An examination device as claimed in claim 4 wherein said selection device selects said one of said images dependent on one of said positioning proposals selected via said operating device.

6. An examination device as claimed in claim 1 further comprising at least one sensor which emits a sensor output identifying a position selected from the group consisting of a current position of said reception unit and a current position of said patient, and wherein said selection device selects one of said images dependent on said sensor output.

7. An examination device as claimed in claim 1 wherein said operating device allows input of a device parameter, and wherein said selection device modifies said one of said images dependent on said device parameter, to produce a modified image, and causes said modified image to be displayed at said display device.

8. An examination device as claimed in claim 7 wherein said operating device allows input of a device parameter selected from the group consisting of a tube voltage of said X-ray source, a tube current of said X-ray source, a switching time of said X-ray source, and a radiation quantity of said X-ray source.

9. An examination device as claimed in claim 7 wherein said selection device modifies a brightness of said one of said images to produce said modified image.

10. An examination device as claimed in claim 7 wherein said selection device modifies a contrast of said one of said images to produce said modified image.

11. An examination device as claimed in claim 7 wherein said selection device modifies said one of said images only in a partial region thereof to produce said modified image.

12. An examination device as claimed in claim 1 further comprising a sensor for producing a sensor output representing an at least two-dimensional image of said patient, and wherein said selection device, from said sensor output, identifies a patient attribute selected from the group consisting of a length of said patient, a thickness of said patient and a sex on said patient, and selects said one of said images dependent on said patient attribute.

13. An examination device as claimed in claim 1 wherein said display device, in addition to said one of said images, displays symbols in relationship to said one of said images representing selectable or controllable device settings.

* * * * *